(12) United States Patent
Dickerson

(10) Patent No.: US 10,159,446 B2
(45) Date of Patent: Dec. 25, 2018

(54) MEDICAL GATING USING POSITIVE AIRWAY PRESSURE DEVICES

(76) Inventor: Gregg A. Dickerson, Lone Tree, CO (US)

( * ) Notice: Subject to any disclaimer, the term of this patent is extended or adjusted under 35 U.S.C. 154(b) by 532 days.

(21) Appl. No.: 13/603,200

(22) Filed: Sep. 4, 2012

(65) Prior Publication Data
US 2014/0066749 A1 Mar. 6, 2014

(51) Int. Cl.
| | |
|---|---|
| *A61B 5/00* | (2006.01) |
| *A61B 5/087* | (2006.01) |
| *A61B 6/00* | (2006.01) |
| *A61M 16/06* | (2006.01) |
| *A61B 6/03* | (2006.01) |
| *G01R 33/567* | (2006.01) |
| *A61M 16/08* | (2006.01) |

(Continued)

(52) U.S. Cl.
CPC ............ *A61B 5/7285* (2013.01); *A61B 5/087* (2013.01); *A61B 5/4836* (2013.01); *A61B 6/032* (2013.01); *A61B 6/4417* (2013.01); *A61B 6/5288* (2013.01); *A61B 6/541* (2013.01); *A61M 16/0051* (2013.01); *A61M 16/0057* (2013.01); *A61M 16/024* (2017.08); *A61M 16/06* (2013.01); *A61M 16/0875* (2013.01); *A61N 5/1039* (2013.01); *A61N 5/1068* (2013.01); *A61B 5/6803* (2013.01); *A61B 6/037* (2013.01); *A61M 2016/0027* (2013.01); *A61M 2016/0033* (2013.01); *A61M 2205/502* (2013.01); *A61N 2005/1052* (2013.01); *A61N 2005/1055* (2013.01); *A61N 2005/1061* (2013.01); *G01R 33/5673* (2013.01)

(58) Field of Classification Search
CPC ..... A61B 5/087; A61B 5/4836; A61B 5/6803; A61B 5/7285; A61B 6/032; A61B 6/037; A61B 6/4417; A61B 6/5288; A61B 6/541; A61M 16/0051; A61M 16/0057; A61M 16/024; A61M 16/06; A61M 16/0875; A61M 2016/0027; A61M 2016/0033; A61M 2205/502; A61N 2005/1052; A61N 2005/1055; A61N 2005/1061; A61N 5/1039; A61N 5/1068; G01R 33/5673

See application file for complete search history.

(56) References Cited

U.S. PATENT DOCUMENTS

| | | | | |
|---|---|---|---|---|
| 4,751,462 A | * | 6/1988 | Glover ............... | G01R 33/5673 324/307 |
| 4,838,259 A | * | 6/1989 | Gluck ............... | A61M 16/0096 128/204.21 |

(Continued)

FOREIGN PATENT DOCUMENTS

WO WO 03003796 A1 * 1/2003 ............. A61B 6/541

OTHER PUBLICATIONS

Lafferty, Keith A, et al. "Rapid Sequence Intubation." MedSape Mar. 23, 2017: 5 pages.

*Primary Examiner* — Michael Rozanski
(74) *Attorney, Agent, or Firm* — Vista IP Law Group, LLP

(57) ABSTRACT

A medical apparatus includes: a breathing device comprising an air pressure generator for generating air pressure, a tube for delivering the air pressure to a patient, and a sensor configured to sense a characteristic associated with a breathing of the patient; and a processing unit configured to receive an output from the sensor, and generate a control signal for controlling a medical device based at least in part on the output from the sensor.

59 Claims, 8 Drawing Sheets

(51) Int. Cl.
*A61M 16/00* (2006.01)
*A61N 5/10* (2006.01)

(56) References Cited

U.S. PATENT DOCUMENTS

| | | | | |
|---|---|---|---|---|
| 5,245,995 | A * | 9/1993 | Sullivan | A61B 5/097 128/204.23 |
| 6,665,555 | B2 * | 12/2003 | Henderson et al. | 600/427 |
| 2005/0145246 | A1 * | 7/2005 | Hartley | A61B 5/0031 128/203.14 |
| 2010/0145358 | A1 * | 6/2010 | Maschke | A61B 17/3403 128/204.25 |
| 2011/0253136 | A1 * | 10/2011 | Sweeney et al. | 128/203.12 |
| 2012/0125337 | A1 * | 5/2012 | Asanoi | 128/204.23 |

* cited by examiner

MEDICAL GATING USING POSITIVE AIRWAY PRESSURE DEVICES

FIELD

This application relates to systems and methods for obtaining breathing signals, and to systems and methods that use the breathing signals.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes during a radiation therapy, the patient may be undergoing breathing motion. In such cases, it may be desirable to monitor the breathing motion of the patient during the treatment delivery session such that radiation may be properly delivered, or ceased to be delivered, to the target region. For example, if the patient's breathing becomes non-periodic (e.g., due to sudden movement such as coughing), then it may be desirable to stop a delivery of radiation.

Applicant of the subject application has determined that it would be desirable to provide a new device and method for obtaining breathing signals, and for determining treatment plans using the breathing signals. Applicant of the subject application has also determined that it would also be desirable to provide a new device and method for performing a medical procedure that accounts for a patient's breathing.

SUMMARY

In accordance with some embodiments, a medical apparatus includes: a breathing device comprising an air pressure generator for generating air pressure, a tube for delivering the air pressure to a patient, and a sensor configured to sense a characteristic associated with a breathing of the patient; and a processing unit configured to receive an output from the sensor, and generate a control signal for controlling a medical device based at least in part on the output from the sensor.

In accordance with other embodiments, a medical method includes: providing a breathing device, the breathing device comprising an air pressure generator for generating air pressure, a tube for delivering the air pressure to a patient, and a sensor; sensing a characteristic of a breathing of the patient using the sensor; and generating a control signal to control a medical device based at least in part on an output from the sensor.

In accordance with other embodiments, a medical apparatus includes: a breathing device configured to provide air pressure, the breathing device comprising an air pressure generator for generating the air pressure, and a tube for delivering the air pressure to a patient; wherein the breathing device comprises a sensor configured to sense a characteristic associated with a breathing of the patient at multiple time points during a breathing cycle of the patient; and a non-transitory medium for storing data associated with the sensed characteristic at the multiple time points.

In accordance with other embodiments, a medical method includes: providing a breathing device, the breathing device comprising an air pressure generator for generating air pressure, a tube for delivering the air pressure to a patient, and a sensor; sensing a characteristic associated with a breathing of the patient using the sensor at multiple time points during a respiratory cycle of the patient; and storing data associated with the sensed characteristic in a non-transitory medium.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
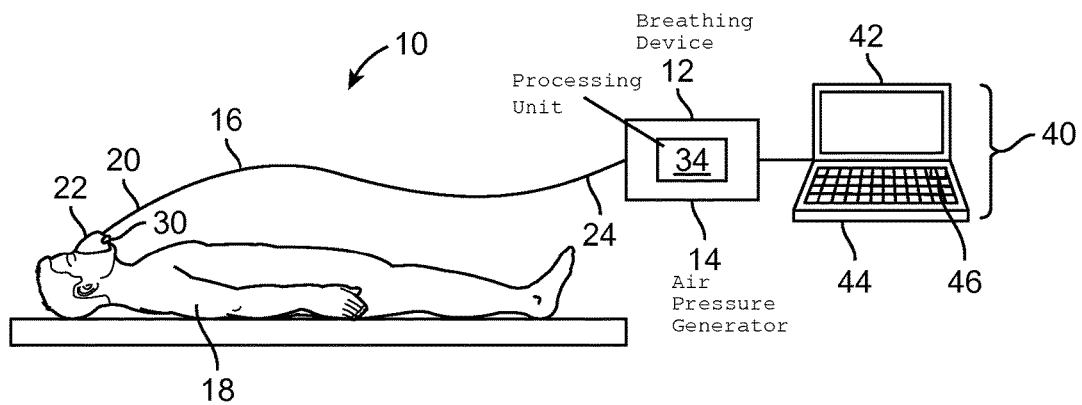
FIG. 1 illustrates a breathing monitoring system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a breathing monitoring system 10 in accordance with some embodiments. The breathing monitoring system 10 includes a breathing device 12 having an air pressure generator 14 for generating air pressure, and a tube 16 for delivering the air pressure to a patient 18. In the illustrated embodiments, the tube 16 has a first end 20 coupled to a facemask 22 worn by the patient 18, and a second end 24 coupled to the air pressure generator 14. As shown in the figure, the breathing monitoring system 10 also includes a sensor 30 configured to sense a characteristic associated with a breathing of the patient 18. By means of non-limiting examples, the characteristic may be an airway pressure, an air flow, etc. In the illustrated embodiments, the sensor 30 is located at the facemask 22. In other embodiments, the sensor 30 may be located anywhere along the length of the tube 16. In further embodiments, the sensor 30 may be located at the air pressure generator 14. In some embodiments, the sensor 30 may be a pressure sensor. In other embodiments, the sensor 30 may be an airflow sensor. In further embodiments, the sensor 30 may be any of other types of sensor that is configured to sense a characteristic associated with a breathing of the patient 18.

It should be noted that as used in this specification, the term "sensor" is not limited to a component that senses a characteristic of a breathing performed by a patient, and may refer to any component that is capable of obtaining any parameter(s) that is associated with a breathing of a patient. For example, in some embodiments in which the sensor 30 is implemented at the air pressure generator 14, the sensor 30 may be any component (such as a signal transmission device) that is capable of obtaining parameter(s) (such as preset pressures, preset airflow rate, etc.) used in the operation of the generator 14. Also, in some embodiments, the sensor 30 may have multiple components. For example, in some embodiments, the sensor 30 may have a sensing component configured to sense a beginning of an inhale state (or an end of an exhale state), and/or an end of an inhale state (or a beginning of an exhale state), and another component (e.g., another sensing component) configured to obtain operation parameter(s) from the generator 14. Similarly, the term "sense" or "sensing" is not necessarily limited to the act of sensing a characteristic of a breathing performed by a patient, and may refer to the act of obtaining parameter(s) used in the operation of the generator 14.

In some embodiments, the breathing device 12 may be implemented using a BPAP machine. A BPAP machine may be configured to deliver positive air pressure cycling between two levels. The cycle times and/or pressure levels may be adjustable (through control(s), such as the user interface 40) for optimal effect and comfort. In some embodiments, the BPAP machine may be configured to provide a controlled air leakage when supporting the patient's breathing through positive airway pressure. In other embodiments, the breathing device 12 may be implemented using a CPAP machine, which is configured to provide a constant positive airway pressure. In further embodiments, the breathing device 12 may be any positive airway pressure device that is configured to support a patient's breathing.

The air pressure generator 14 includes a processing unit 34 configured to generate a signal to activate a generator to thereby generate air pressure within the tube 16. The facemask 22 is configured to provide a seal at the interface between the patient's face and the perimeter of the facemask 22 so that air pressure generated within the tube 16 is delivered into the airway of the patient 18. The processing unit 34 of the generator 14 may include circuit. For example, the processing unit 34 may be one or more processors in some embodiments. The processing unit 34 may further include software running on the processor(s) in some embodiments. The processor may be a FPGA processor, an ASIC processor, a general purpose processor, or any of other types of processor.

The breathing monitoring system 10 also includes a user interface 40 having a screen 42 for displaying information to a user, and an input device 44 for allowing the user to input information, such as user commands. The user interface 40 is communicatively coupled to the air pressure generator 14, so that information derived from signals from the air pressure generator 14 and/or from the sensor 30 may be displayed on the screen 42 for viewing by the user. In some embodiments, the input device 44 may be used to control the air pressure generator 14, and/or to prescribe the manner in which the patient's breathing may be monitored. For example, in some embodiments, the input device 44 may be used to set the amount of airway pressure desired, sensitivity of the breathing device 12, and/or to prescribe the sampling rate for the sensor 30. The user interface 40 also includes a non-transitory medium 46 for storing information derived from the operation of the breathing device 12. For example, the non-transitory medium 46 may be configured to store signals transmitted from the sensor 30, and/or data derived from the signals transmitted from the sensor 30. The non-transitory medium 46 may also store operating parameters that are used in the operation of the air pressure generator 14 in some embodiments.

In some embodiments, the user interface 40 may be implemented using a computer (such as a desktop or a laptop). In other embodiments, the user interface 40 may be implemented using a handheld device, such as an iPad, a tablet, an iPhone, a smart phone, etc. In either case, the user interface 40 will include processing unit therein for processing information. In other embodiments, the user interface 40 may be implemented as a part of the air pressure generator 14. In such cases, the processing unit 34 of the air pressure generator 14 may also be considered the processing unit for the user interface 40. As used in this specification, the term "processing unit" (such as the processing unit 34) may refer to one or more processing units, which may reside in one component (e.g., the air pressure generator 14, or in the user interface 40), may reside in multiple respective components (e.g., the air pressure generator 14 and the user interface 40), or may be communicatively coupled to one or more components (e.g., the air pressure generator 14, the user interface 40, etc.).

Figure 2:
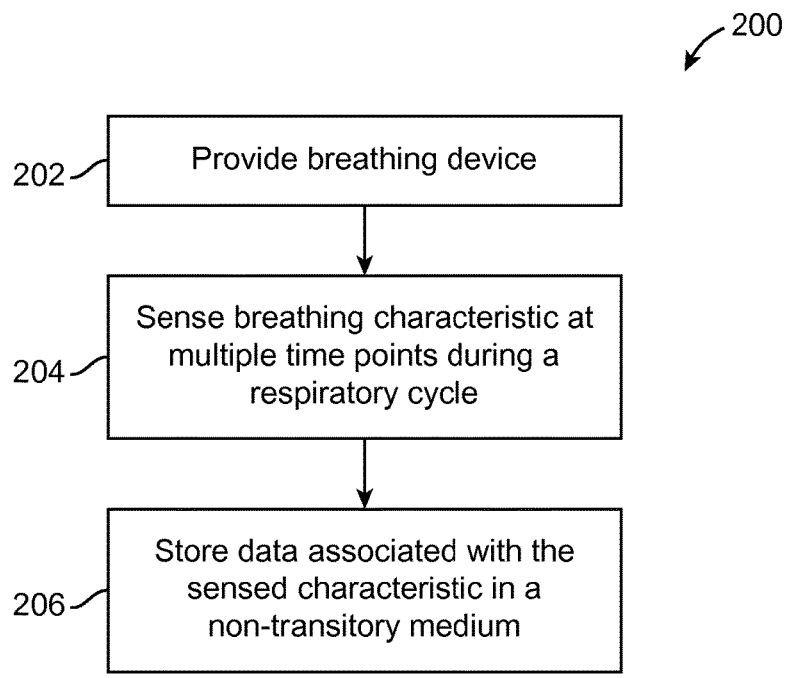
FIG. 2 illustrates a method of obtaining and processing breathing signals in accordance with some embodiments.

FIG. 2 illustrates a method 200 performed using the breathing monitoring system 10 of FIG. 1 in accordance with some embodiments. First, a breathing device is provided (Item 202). The breathing device may be the breathing device 12, which includes the air pressure generator 14 for generating air pressure, the tube 16 for delivering the air pressure to the patient 18, the facemask 22, and the sensor 30. During use, the facemask 22 is placed over the patient's mouth, and the perimeter of the facemask 22 forms a seal with the patient's skin. An inhale sensor (not shown), which may be located at the facemask 22, at the tube 20, or at the air pressure generator 14, is configured to sense an inhaling being performed by the patient 18, and generate an inhale signal in response thereto. The inhale signal is transmitted to the air pressure generator 14, which generates air pressure within the tube 16 in response to the inhale signal from the inhale sensor. The tube 16 supplies the air pressure to the airway of the patient 18, thereby assisting the patient 18 in the breathing. In some embodiments, the inhale sensor for sensing the inhaling of the patient 18 may be the sensor 30, or another sensor that is different from the sensor 30. The sensor for sensing the inhaling of the patient 18 may be an air flow sensor, a pressure sensor, or any of other types of sensor that is configured to sense a characteristic associated with an inhaling.

While the patient 18 is breathing, a characteristic associated with the breathing of the patient 18 is sensed using the sensor 30 at multiple time points during a respiratory cycle of the patient 18 (Item 204). In some embodiments, the sensor 30 is a pressure sensor, and multiple pressure values are obtained at different respective time points during the respiratory cycle of the patient 18. In other embodiments, the sensor 30 is an airflow sensor, and multiple airflow values are obtained at different respective time points during the respiratory cycle of the patient 18. In further embodiments, the sensor 30 may be any of other types of sensor, and multiple characteristic values are obtained at different respective time points during the respiratory cycle of the patient 18.

Next, the method 200 includes storing data associated with the sensed characteristic in a non-transitory medium (Item 206). In some embodiments, the non-transitory medium may be the non-transitory medium 46 in the system 10 of FIG. 1. In other embodiments, the non-transitory medium may be a storage device that is a part of the air pressure generator 14. In further embodiments, the non-transitory medium may be communicatively coupled to the air pressure generator 14, the sensor 30, and/or the user interface 40. Also, in some embodiments, the stored data may be values of the respective signals obtained from the sensor 30. In other embodiments, the stored data may be data derived (e.g., through processing by the processing unit 34) from the values of the signals obtained from the sensor 30.

In some embodiments, the data stored may be airway pressure values and corresponding time points at which the respective airway pressure values are obtained. In other embodiments, the data stored may be airflow values and corresponding time points at which the respective airflow values are obtained. In further embodiments, the data stored may be other characteristic values and corresponding time points at which the respective characteristic values are obtained.

In other embodiments, instead of, or in addition to, storing the data in a non-transitory medium, the processing unit 34 may process signals (an example of breathing signals) from the sensor 30 to thereby monitor the breathing of the patient 20. For example, the processing unit 34 may be configured to determine whether the patient 18 is breathing regularly based on the signals from the sensor 30. In some embodiments, the signals from the sensor 30 and/or results of the processing of the sensor signals may be displayed on the monitor 42, for allowing a user to view them.

Also, in some embodiments, if data obtained using the sensor 30 are stored, the data may be reviewed subsequently. For example, in some embodiments, the stored data may be analyzed (e.g., using a computer) to determine a treatment plan that considers a patient's breathing. By means of non-limiting examples, the treatment plan may be a radiation treatment plan, a proton treatment plan, or any of other types of treatment plan that may consider a patient's breathing during execution of the treatment. In some embodiments, when determining a treatment plan, treatment parameters may be determined using the computer, and may be stored in a non-transitory medium.

Figure 3:
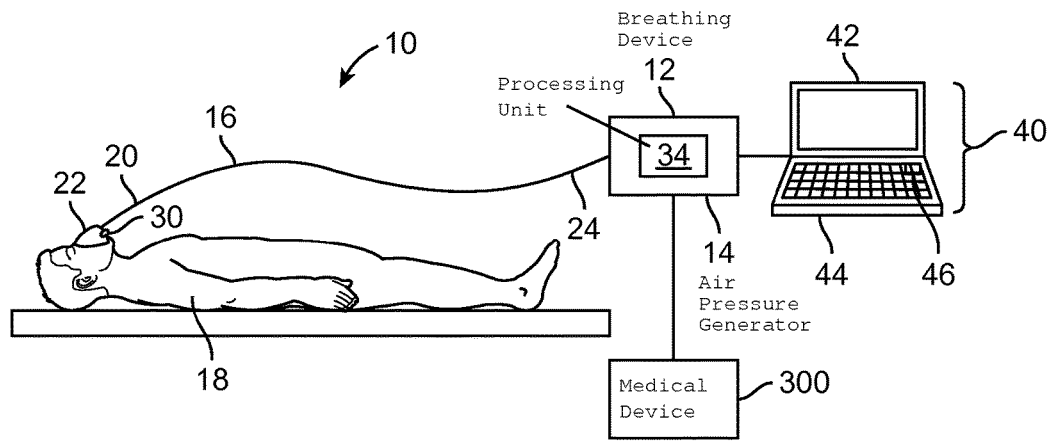
FIG. 3 illustrates the breathing monitoring system of FIG. 1, particularly showing the system being used with a medical device in accordance with some embodiments.

In other embodiments, the breathing monitoring system 10 may be used with a medical device. FIG. 3 illustrates the breathing monitoring system 10 of FIG. 1 that is used with a medical device 300. In the illustrated embodiments, the medical device 300 is communicatively coupled to the airway pressure generator 14. In other embodiments, the medical device 300 may be communicatively coupled to the sensor 30 (e.g., directly to the sensor 30, or indirectly through another component, such as another processing unit) without going through the airway pressure generator 14.

Figure 4:
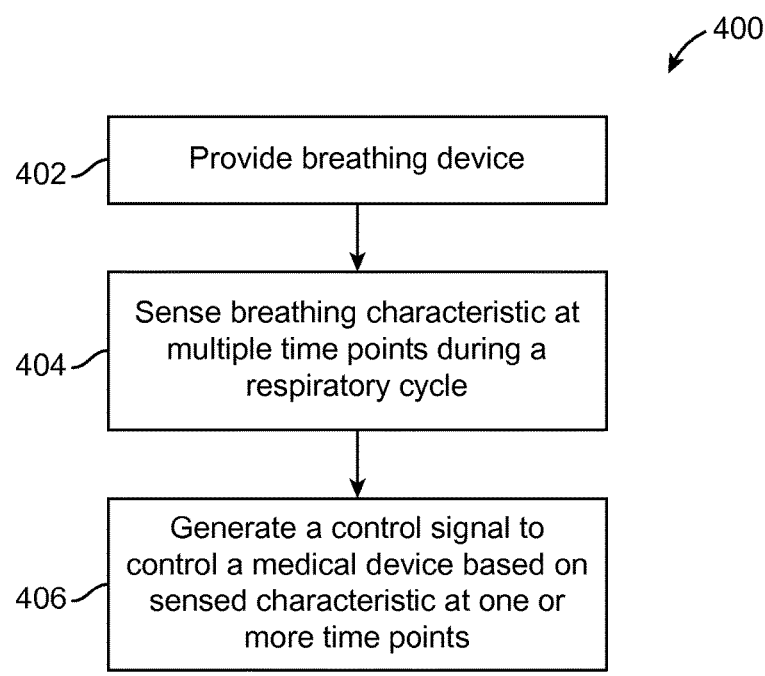
FIG. 4 illustrates a method of using the breathing monitoring system of FIG. 1 to control a medical device in accordance with some embodiments.

FIG. 4 illustrates a method 400 of controlling a medical device performed using the breathing monitoring system 10 of FIG. 1 in accordance with some embodiments. First, a breathing device is provided (Item 402). The breathing device may be the breathing device 12, which includes the air pressure generator 14 for generating air pressure, the tube 16 for delivering the air pressure to the patient 18, the facemask 22, and the sensor 30. During use, the facemask 22 is placed over the patient's mouth, and the perimeter of the facemask 22 forms a seal with the patient's skin. An inhale sensor (not shown), which may be located at the facemask 22, at the tube 20, or at the air pressure generator 14, is configured to sense an inhaling being performed by the patient 18, and generate an inhale signal in response thereto. The inhale signal is transmitted to the air pressure generator 14, which generates air pressure within the tube 16 in response to the inhale signal from the inhale sensor. The tube 16 supplies the air pressure to the airway of the patient 18, thereby assisting the patient 18 in the breathing. In some embodiments, the inhale sensor for sensing an inhaling of the patient 18 may be the sensor 30, or another sensor that is different from the sensor 30. The sensor for sensing the inhaling of the patient 18 may be an air flow sensor, a pressure sensor, or any of other types of sensor that is configured to sense a characteristic associated with an inhaling.

While the patient 18 is breathing, a characteristic associated with the breathing of the patient 18 is sensed using the sensor 30 at multiple time points during a respiratory cycle of the patient 18 (Item 404). In some embodiments, the sensor 30 is a pressure sensor, and multiple pressure values are obtained at different respective time points during the respiratory cycle of the patient 18. In other embodiments, the sensor 30 is an airflow sensor, and multiple airflow values are obtained at different respective time points during the respiratory cycle of the patient 18. In further embodiments, the sensor 30 may be any of other types of sensor, and multiple characteristic values are obtained at different respective time points during the respiratory cycle of the patient 18.

Based on the sensed characteristic at one or more of the time points, the processing unit 34 and/or the processing unit 46 then generates a control signal to control the medical device 300 (Item 406).

In some embodiments, the signals from the sensor 30 may be processed by the processing unit 34 to determine a corresponding breathing phases. In some embodiments, the sensor 30 may be a flow sensor, in which cases, the flow signals from the sensor 30 may be represented by the flow signal graph 500 shown in FIG. 5A. The flow signals represent the amount or rate of air flow being supplied at different points in time. The flow signal graph 500 may be obtained by plotting values of sensor signals against time at which the sensor signals are obtained from the sensor 30. In some embodiments, each of the flow signals in the flow diagram 500 may be obtained by sensing characteristic (e.g., airflow) due to a breathing performed by a patient. In other embodiments, part(s) of the flow diagram 500 may be obtained using information (e.g., operation parameter(s)) from the generator 14. For example, in some embodiments, the timing of when the various parts of the diagram 500 begin and end may be determined by sensing breathing characteristics, while the values (and therefore the shape) of the flow curve may be obtained from the generator 14 (e.g., they may be obtained directly from the generator 14, or may be derived using information, such as operation parameter(s) obtained from the generator 14). In some cases, the operation parameter may be a flow rate set in the generator 14, which may correspond with the actual flow rate experienced by the patient.

As shown in the figure, a certain signal value 502 that is obtained when the patient is at a beginning of an inhale phase may be associated with a beginning 532 of a respiratory cycle in a phase diagram 530, and a certain signal value 504 that is obtained when the patient is at an end of an exhale phase may be associated with an end 534 of the respiratory cycle in the phase diagram 530. The phase of a physiological cycle represents a degree of completeness of a physiological cycle. In some embodiments, the phases of a respiratory cycle may be represented by a phase variable having values between 0° and 360°, like that shown in the phase diagram 530. For example, a phase value of 0° (and 360°) may represent a beginning of an inhale state (or an end of an exhale state), and the phase value varies linearly between 0° and 360° in a physiological cycle. As shown in the diagram, for each point in the sensor value graph 500 at certain point in time, a corresponding phase value at the same point in time may be obtained. Thus, for each sensor signal, the processing unit can determine the corresponding phase of the respiratory cycle. In some embodiments, the determined phase may be considered an example of a breathing signal. In other embodiments, the sensor signal itself may be considered an example of a breathing signal. As shown in the figure, the phase values collectively form the phase diagram 530 that includes a plurality of data points, with each of the data points having a phase value and a time value.

In other embodiments, the processing unit 34 may be configured to determine lung volume during a respiratory cycle. As shown in the lung volume diagram 510 in FIG. 5A, the lung volume may be determined by summing the area under the flow diagram over time. The lung volume has a peak 512 representing an end of an inhale state, and a minimum value 514 representing an end of an exhale state (or a beginning of an inhale state). Using the points 514 at different respective respiratory cycles, the phase diagram 530 may be determined by associating the points 514 with the 0° and 360° phase values at the different corresponding time points.

Figure 5A:
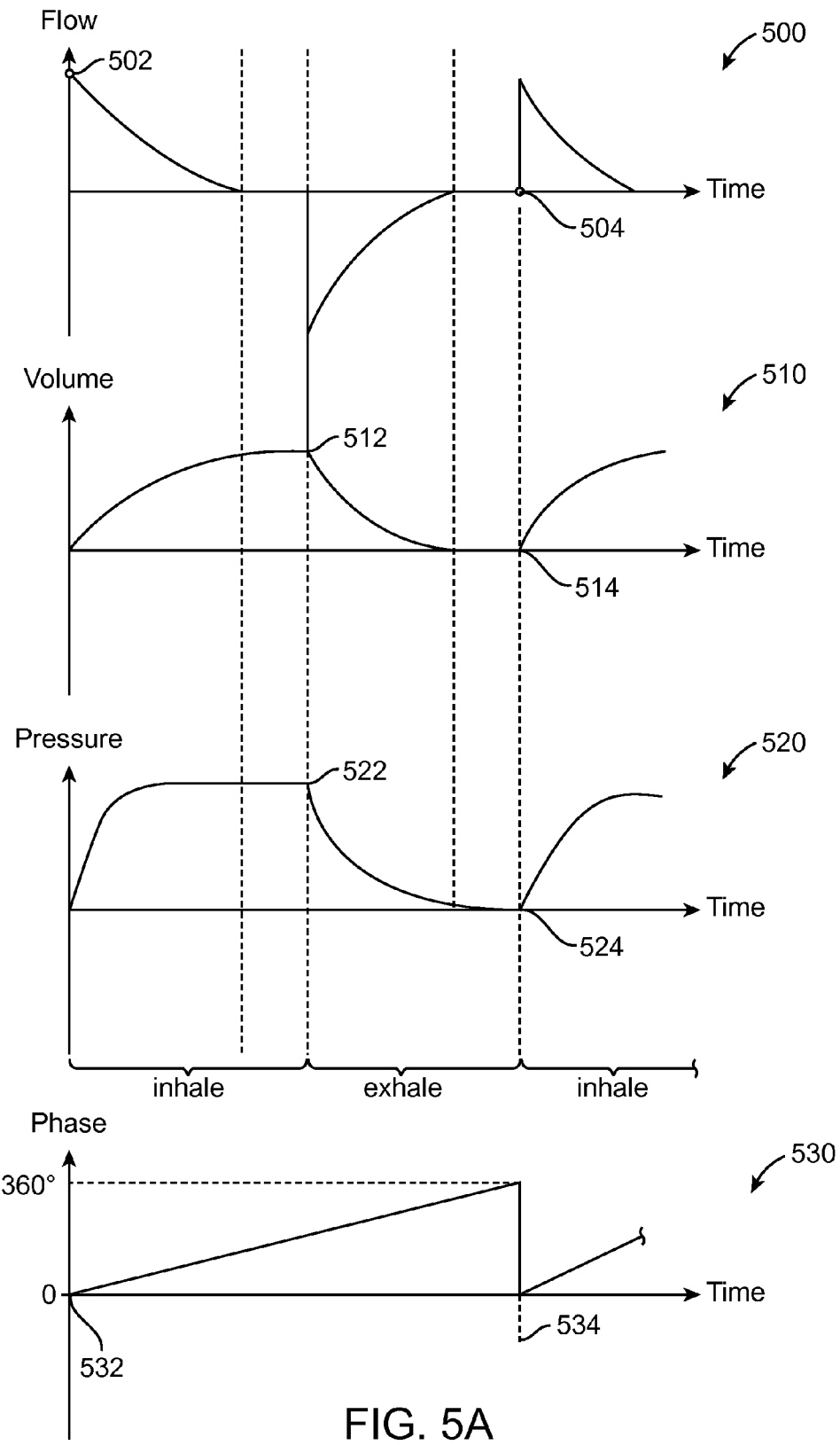
FIG. 5A illustrates different breathing characteristic graphs aligned with a corresponding breathing phase diagram in accordance with some embodiments.

In further embodiments, the sensor 30 may be a pressure sensor for sensing pressure associated with an airway (which may be pressure in the tube 16, pressure in the facemask 22, or pressure in the airway of the patient). In such cases, the sensor 30 may provide sensed pressure values at different time points during a respiratory cycle. FIG. 5A illustrates a pressure diagram 520 representing pressure values that may be provided by the sensor 30 at different respective time points. The pressure has a peak 522 representing an end of an inhale state, and a minimum value 524 representing an end of an exhale state (or a beginning of an inhale state). Using the points 524 at different respective respiratory cycles, the phase diagram 530 may be determined by associating the points 524 with the 0° and 360° phase values at the different corresponding time points.

In some embodiments, each of the pressure signals in the pressure diagram 520 may be obtained by sensing characteristic (e.g., pressure) due to a breathing performed by a patient. In other embodiments, part(s) of the pressure diagram 520 may be obtained using information (e.g., operation parameter(s)) from the generator 14. For example, in some embodiments, the timing of when the various parts of the diagram 520 begin and end may be determined by sensing breathing characteristics, while the values (and therefore the shape) of the pressure curve may be obtained from the generator 14 (e.g., they may be obtained directly from the generator 14, or may be derived using information, such as operation parameter(s) obtained from the generator 14). In some cases, the operation parameter may be a pressure set in the generator 14, which may correspond with the actual airflow pressure experienced by the patient.

In other embodiments, the processing unit 34 may determine breathing amplitude values that correspond with respective sensor signal values. In some embodiments, the sensor 30 may be a flow sensor, in which cases, the flow signals from the sensor 30 may be represented by the flow signal graph 500 shown in FIG. 5B. The flow signals represent the amount or rate of air flow being supplied at different points in time. The flow signal graph 500 may be obtained by plotting values of sensor signals against time at which the sensor signals are obtained from the sensor 30. As shown in the figure, a certain signal value 506 that is obtained when the patient is at an end of an inhale phase may be associated with an amplitude peak 542 in an amplitude diagram 540, and a certain signal value 504 that is obtained when the patient is at an end of an exhale phase may be associated with a minimum amplitude value 544 in the amplitude diagram 540. The amplitude values in the amplitude diagram 540 may represent breathing motion, such as a motion of a diaphragm, a motion of a chest, as the patient is breathing. As shown in the diagram, for each point in the sensor value graph 500 at certain point in time, a corresponding amplitude value at the same point in time may be obtained. Thus, for each sensor signal, the processing unit can determine the corresponding amplitude in the respiratory cycle. In some embodiments, the determined amplitude may be considered an example of a breathing signal. In other embodiments, the sensor signal itself may be considered an example of a breathing signal. As shown in the figure, the amplitude values collectively form the amplitude diagram 540 that includes a plurality of data points, with each of the data points having an amplitude value and a time value.

In other embodiments, the processing unit 34 may be configured to determine lung volume during a respiratory cycle. As shown in the lung volume diagram 510 in FIG. 5B, the lung volume may be determined by summing the area under the flow diagram over time. The lung volume has a peak 512 representing an end of an inhale state, and a minimum value 514 representing an end of an exhale state (or a beginning of an inhale state). Using the points 512, 514 at different respective respiratory cycles, the amplitude diagram 540 may be determined by associating the points 512, 514 with the maximum and minimum values 542, 544 at the different corresponding time points.

Figure 5B:
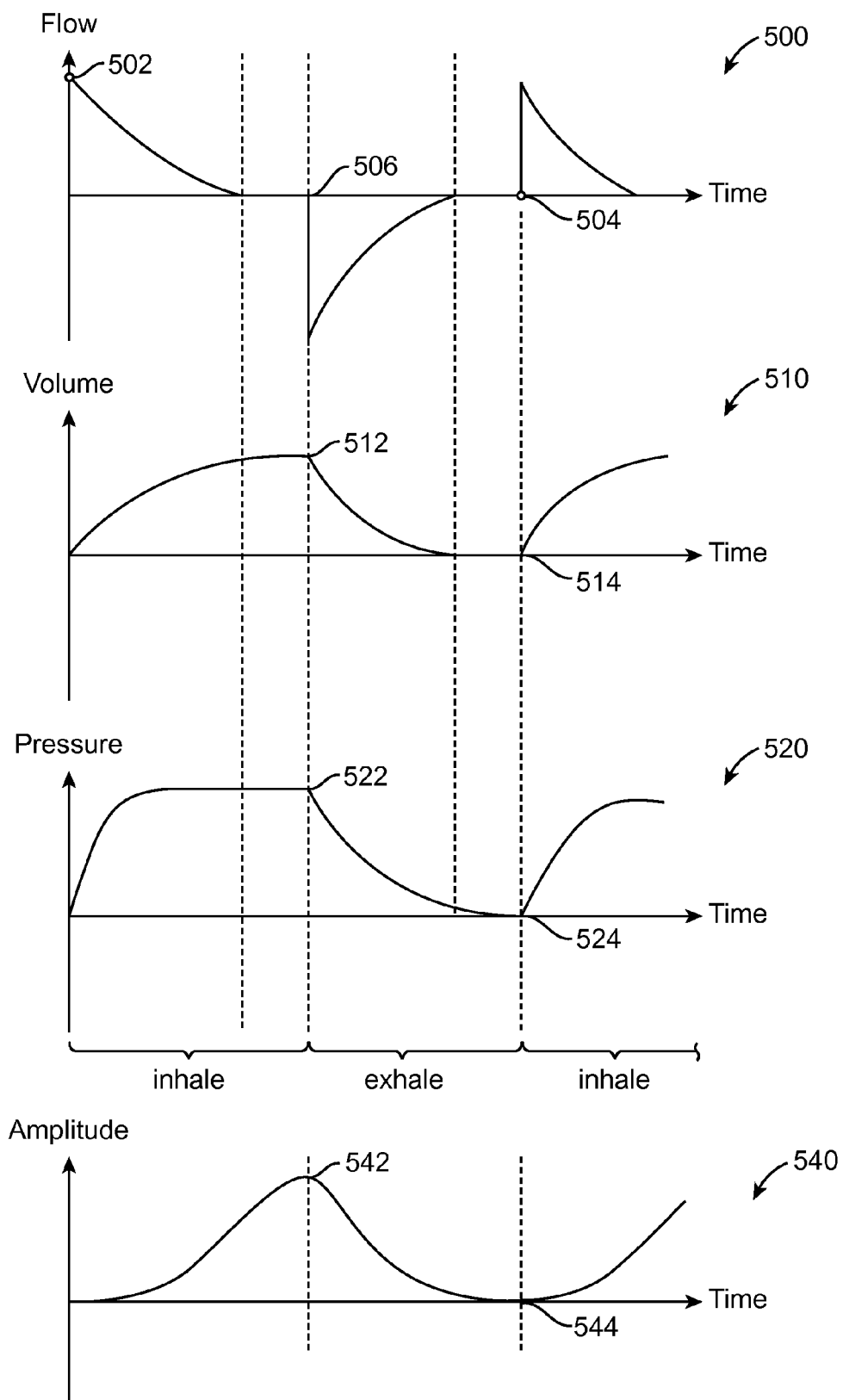
FIG. 5B illustrates different breathing characteristic graphs aligned with a corresponding breathing amplitude diagram in accordance with some embodiments.

In further embodiments, the sensor 30 may be a pressure sensor for sensing pressure associated with an airway (which may be pressure in the tube 16, pressure in the facemask 22, or pressure in the airway of the patient). In such cases, the sensor 30 may provide sensed pressure values at different time points during a respiratory cycle. FIG. 5B illustrates a pressure diagram 520 representing pressure values that may be provided by the sensor 30 at different respective time points. The pressure has a peak 522 representing an end of an inhale state, and a minimum value 524 representing an end of an exhale state (or a beginning of an inhale state). Using the points 524 at different respective respiratory cycles, the amplitude diagram 540 may be determined by associating the points 522, 524 with the maximum and minimum values 542, 544 at the different corresponding time points.

In further embodiments, a device (such as a strain gauge, or a camera) for determining a breathing amplitude of the patient may be employed to determine breathing amplitudes as the patient is breathing. This is performed at the same time the sensor 30 is being used to sense breathing characteristic of the patient. Thus, for each sensor signal obtained using the sensor 30, the processing unit 34 can determine the corresponding breathing amplitude (e.g., by looking up sensor signal and amplitude signal that are both obtained at the same time).

It should be noted that the flow diagram 500, the volume diagram 510, and the pressure diagram 520 are not limited to the examples shown in FIGS. 5A-5B, and that these diagrams may have different shapes from those shown in the above examples. Also, in the above embodiments, the processing unit has been described as processing output from the sensor 30 to determine a metric (e.g., a phase, or an amplitude) of a breathing state. In other embodiments, the metric determined by the processing unit using output from the sensor 30 may be a flow (like that shown in the flow diagram 500), a volume (like that shown in the volume diagram 510), or a pressure (like that shown in the pressure diagram 520). In further embodiments, the processing unit may be configured to process the output from the sensor 30 to determine other types of metric that represents a breathing state.

Figure 6:
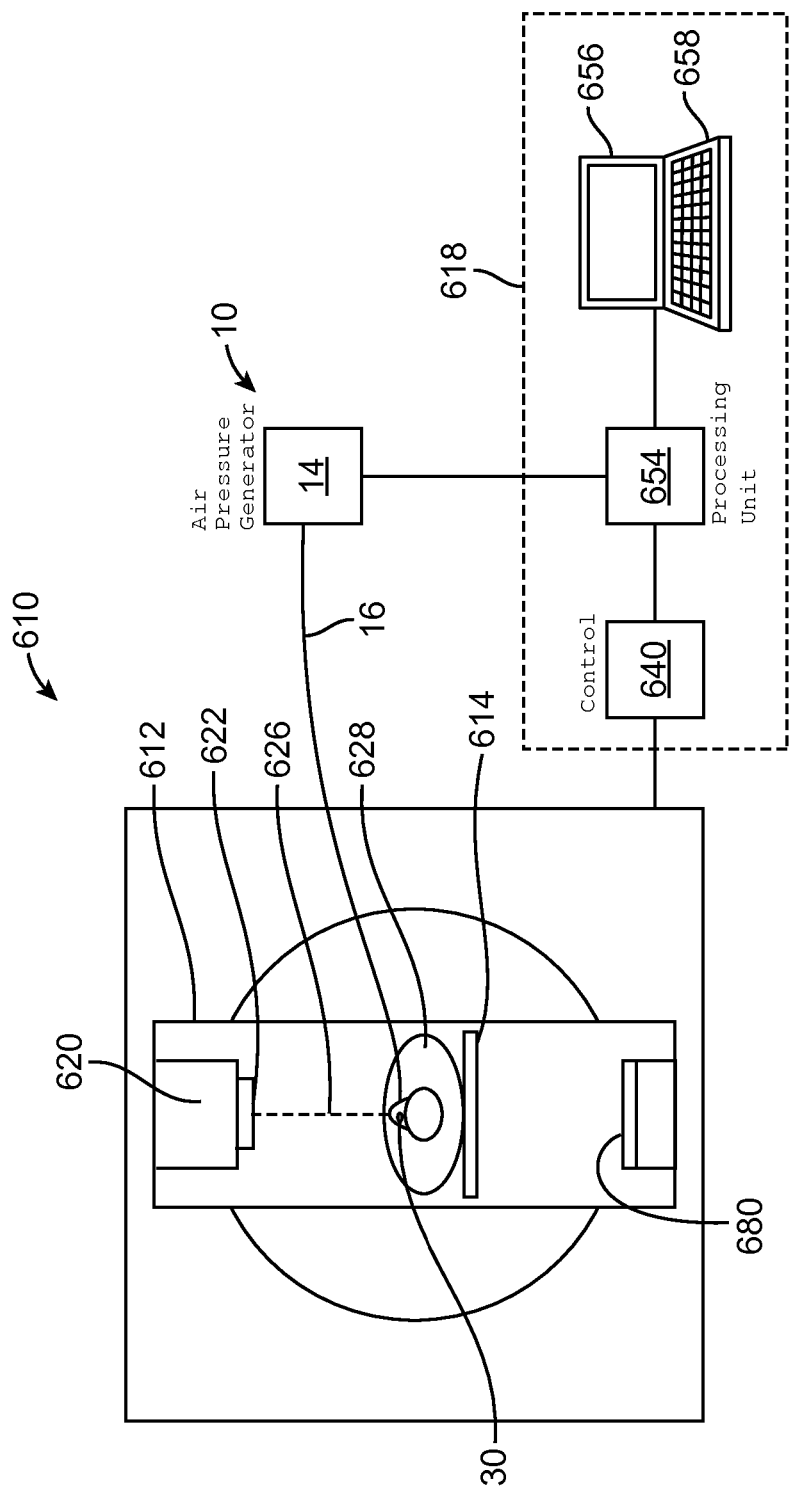
FIG. 6 illustrates a radiation system that uses the breathing monitoring system of FIG. 1 in accordance with some embodiments.

The breathing monitoring system 10 and the methods described previously may be used with a variety of medical devices, and in various different medical procedures. In some embodiments, the medical device 300 may be a radiation treatment machine. FIG. 6 illustrates a radiation system 610 that is used with the breathing monitoring system 10. The system 610 is a treatment system that includes a gantry 612, a patient support 614 for supporting a patient, and a control system 618 for controlling an operation of the gantry 612. The gantry 612 is in a form of an arm. The system 610 also includes a radiation source 620 that projects a beam 626 of radiation towards a patient 628 while the patient 628 is supported on support 614, and a collimator system 622 for controlling a delivery of the radiation beam 626. The radiation source 620 can be configured to generate a cone beam, a fan beam, or other types of radiation beams in different embodiments.

In the illustrated embodiments, the radiation source 620 is a treatment radiation source for providing treatment energy. In other embodiments, in addition to being a treatment radiation source, the radiation source 620 can also be a diagnostic radiation source for providing diagnostic energy for imaging purpose. In such cases, the system 610 will include an imager, such as the imager 680, located at an operative position relative to the source 620 (e.g., under the support 614). In further embodiments, the radiation source 620 may be a treatment radiation source for providing treatment energy, wherein the treatment energy may be used to obtain images. In such cases, in order to obtain imaging using treatment energies, the imager 680 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 620 is able to generate X-ray radiation at a plurality of photon energy levels within a range anywhere between approximately 10 keV and approximately 20 MeV. In further embodiments, the radiation source 620 can be a diagnostic radiation source. In the illustrated embodiments, the radiation source 620 is coupled to the arm gantry 612. Alternatively, the radiation source 620 may be located within a bore.

In the illustrated embodiments, the control system 618 includes a processing unit 654, such as a processor, coupled to a control 640. The control system 618 may also include a monitor 656 for displaying data and an input device 658, such as a keyboard or a mouse, for inputting data. The operation of the radiation source 620 and the gantry 612 are controlled by the control 640, which provides power and timing signals to the radiation source 620, and controls a rotational speed and position of the gantry 612, based on signals received from the processing unit 654. Although the control 640 is shown as a separate component from the gantry 612 and the processing unit 654, in alternative embodiments, the control 640 can be a part of the gantry 612 or the processor 654. The processing unit 654 may be the processing unit 34 of the breathing monitoring system 10 of FIG. 1, or a separate processing unit that is different from the processing units 34. Also, in some embodiments, the screen 656 may be the screen 42 of the breathing monitoring system 10 of FIG. 1, and the input device 658 may be the input device 44 of FIG. 1. In other embodiments, the screen 656 and the input device 658 may be different from the screen 42 and the input device 44 of FIG. 1.

In some embodiments, when using the system 610 of FIG. 6, the radiation source 620 is rotated about the patient 628 to deliver treatment radiation from a plurality of gantry angles, for example, as in arc therapy. As treatment radiation is being delivered to the patient 628, the breathing monitoring system 10 of FIG. 1 may be used to monitor the breathing of the patient 628. In some embodiments, the processing unit 654 processes the signals from the sensor 30 to determine breathing states of the patient 628, and then gates the delivery of the treatment radiation in real time based on the breathing states. For example, the processing unit 654 may process signals from the sensor 30 to determine respiratory amplitudes of the patient 628, and then gates the delivery of the treatment radiation based on the respiratory amplitudes. In such cases, the processing unit 654 may cause the radiation source 620 to deliver radiation, or to stop a delivery of radiation, when the determined amplitude is within a prescribed amplitude range. In other embodiments, the processing unit 654 processes the signals from the camera to determine respiratory phases of the patient 628, and then gates the delivery of the treatment radiation based on the respiratory phases. For example, the processing unit 654 may cause the radiation source 620 to deliver radiation, or to stop a delivery of radiation, when the determined phase is within a prescribed phase range. In further embodiments, the processing unit 654 processes the signals from the sensor 30 to detect non-periodicity, and then gates the delivery of the treatment radiation based on the detection of non-periodicity. In other embodiments, instead of, or in addition to, controlling the delivery of radiation, the processing unit 654 may be configured to control the gantry 612 (e.g., stop, accelerate, or decelerate the gantry 612), to operate the collimator system 622, to position the patient support 614, and/or to adjust a dose rate (e.g., increase a dose rate or decrease a dose rate), based on the sensor values obtained using the sensor 30 (e.g., based directly on the sensor values, based on amplitude and/or phase determined using the sensor value(s), based on detection of non-periodicity, etc.). Thus, the signals from the sensor 30 may be used to control one or more components of a radiation system in synchronization with a breathing of the patient 628. In some embodiments, the adjustment of dose rate may involve controlling a collimator and/or a gantry to which the radiation source is mounted. Also, in some embodiments, the dose rate adjustment may be an adjustment of a rate of radiation exposure, a rate of image acquisition, or both. In further embodiments, based on signals from the sensor 30, the processing unit may be configured to control an image process, such as an image data collection process, an image reconstruction process, a process for binning image data, etc.

During the treatment process, the processing unit 654 monitors the patient's 628 breathing, and correlates feature(s) of the breathing (such as sensor signals, breathing amplitudes, breathing phases, etc.) with positions of internal target region that is being irradiated by the radiation beam 626. For example, based on signals received from the sensor 30, the processing unit 654 then determines the phase/amplitude of the breathing cycle. The phase of the breathing cycle or the amplitude is then used by the processing unit 654 to determine a position of the internal target region based on a pre-established relationship between breathing phase/amplitude and position of internal target region. In some embodiments, the relationship between the breathing phase/amplitude and target position may be pre-determined by a physician during a treatment planning process. For example, during a treatment planning process, it may be determined that when a patient is at breathing phase=40° (or when a sensor value from the sensor 30 is 4.5), the corresponding position of the internal target region is at position X=45 mm, Y=23 mm, and Z=6 mm relative to the isocenter. This technique allows the treatment radiation system 610 to target delivery of radiation towards the target region based on breathing signals obtained by the system 10. Thus, it has the benefit of obviating the need to continuously or periodically imaging the internal target region using X-ray imaging, which may be harmful to the patient due to its additional radiation dose.

In other method of using the system 10 with the radiation system 610, the processing unit 654 is configured to detect non-periodicity in the patient's 628 breathing based on signals received form the sensor 30. When the processing unit 654 determines that there is non-periodicity in the patient's 628 breathing, the processing unit 654 may generate a signal (e.g., a beam-stop signal) to cause the radiation source 620 to stop delivering radiation, and/or a signal to control a motion of the gantry 612 (e.g., to stop the gantry, decelerate the gantry 612, or accelerate the gantry 612).

Figure 7:
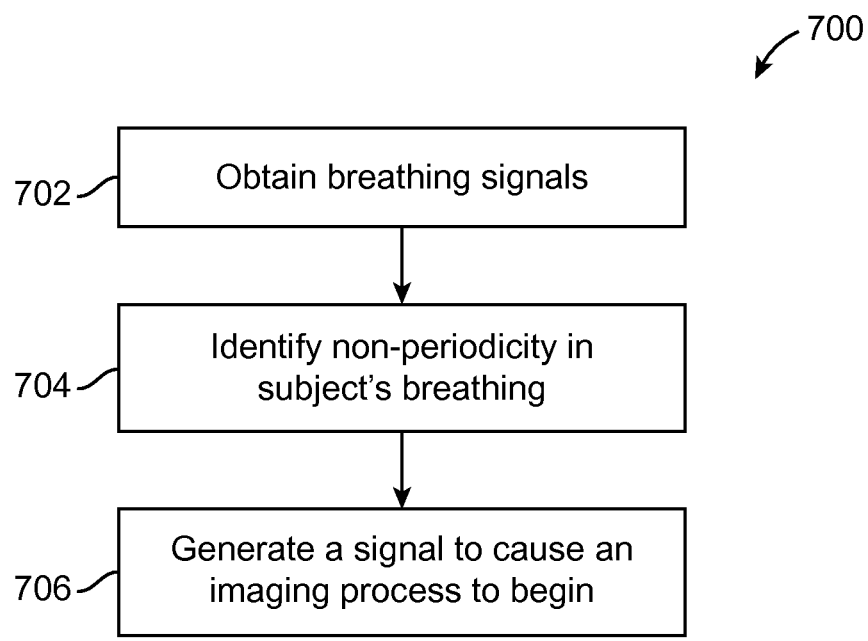
FIG. 7 illustrates a method of triggering an imaging procedure in accordance with some embodiments.

In other embodiments, as an alternative, or in addition, to controlling component(s) of the radiation system 610, if the radiation system 610 has imaging capability, the processing unit 654 may be configured to generate a signal to trigger an imaging process to image the internal target region when the processing unit 654 determines that there is non-periodicity in the patient's 628 breathing based on signals received from the sensor 30. FIG. 7 illustrates a method 700 of triggering an imaging process in accordance with some embodiments. In the method 700, the processing unit 654 obtains signals (breathing signals) from the sensor 30 (step 702), and the processor 654 then analyzes the signals to identify a non-periodicity in a subject's breathing (step 704).

When the processing unit 654 determines that there is non-periodicity in the patient's 628 breathing based on signals from the sensor 30, the processing unit 654 then generates a signal to cause an image process to begin (706). In the illustrated embodiments, if the radiation system 610 has imaging capability (e.g., if the radiation system 610 has the imager 680), the image process may be performed by the system 610. For example, the radiation source 620 may deliver imaging radiation having diagnostic energy (e.g., in kv range), or radiation having treatment energy level (e.g., in MeV range) to generate one or more images of the internal region using the imager 680. Alternatively, a separate imaging system may be used to generate the image(s) of the internal region. For example, the separate imaging system may be a CT system, an x-ray system, an ultrasound imaging device, a MRI system, a tomosynthesis imaging system, a PET system, a SPECT system, or any other system that is capable of obtaining an image of the internal target region. In further embodiments, the radiation system 610 may have two imagers (e.g., at 90° or another angle apart from each other). In such cases, the processing unit 654 may generate the signal to cause an image process to be performed using the two imagers.

In some embodiments, the image(s) of the internal target region is used by the processing unit 654 to verify the position of the target region, and/or to confirm the pre-established relationship between breathing feature (amplitude, phase, etc.) and target position. In other embodiments, the image of the internal target region may also be used by the processing unit 654 to verify the relationship between breathing feature and target position (e.g., external-internal correlation model). If a result of the verification process indicates that the model is inaccurate, the processing unit 654 may update (e.g., modify, recreate, etc.) the relationship between breathing feature and target position (e.g., external-internal correlation model) in the treatment plan, so that the updated relationship may be used by the system 610 to deliver additional radiation to the patient 628 (e.g., to control the radiation source, collimator, gantry, and/or patient support). Thus, in some embodiments, signals from the sensor 30 may be used to determine a treatment plan in real time during a treatment session. In other embodiments, the processing unit 654 may cause the radiation process to stop if the result of the verification process indicates that the model is inaccurate.

In other embodiments, the image(s) of the internal target region determined from the method 700 may be used by the processing unit 654 to determine the position of the internal target region using stereo imaging technique. In stereo imaging technique, a set of reference images are first obtained. The reference images may be obtained before the treatment process begins. Each of the reference images is obtained when the internal target region is at a certain position, and therefore, each reference image is associated with a certain position of the target region. In some embodiments, the reference images may be generated using a CT system by rotating the radiation source of the CT system at different gantry angles while the target is undergoing motion. Thus, the reference images are obtained at different times. In other embodiments, if the system 610 has imaging capability, the reference images may be generated using the system 610. In some embodiments, after the image (input image) from the method 700 is obtained, the processing unit 654 then selects one or more reference images from the reference image set that spatially correspond with the input image. In one technique, the processing unit 654 determines a projection line that extends between the source that generates the input image and the target image in the image frame. The processing unit 654 also determines a plurality of projection lines for respective reference images, wherein each projection line extends between the source and the target image in the corresponding reference image. The processing unit 654 then determines, for each projection line, an epipolar distance that is between the projection line of the input image and the projection line for the corresponding reference image. The epipolar distance is measured in a direction that is perpendicular to both the projection line of the input image and the projection line of the reference image. In some embodiments, the processing unit 654 is configured to select a reference image that spatially corresponds with the input image by comparing the epipolar distances with a prescribed threshold. If the epipolar distance for a reference image is below the prescribed threshold, then it may be determined that the target's position when the input image is generated (during method 700) corresponds (e.g., is the same relative to certain arbitrary coordinate system) with the target's position when the reference image is generated. In such cases, the processing unit 654 then selects such reference image for determining the position of the target region. In some embodiments, the position of the midpoint at the epipolar line between the projection line of the input image and the projection line of the selected reference image may be used as the position of the target. Stereo imaging technique has been described in U.S. patent application Ser. No. 12/211,686, filed on Sep. 16, 2008, the entire disclosure of which is expressly incorporated by reference herein.

It should be noted that using detected non-periodicity of patient's breathing to trigger an imaging of internal region is advantageous because it obviates the need to periodically image the internal region for verification of the position of the internal region and for verification of the relationship between breathing and target positions. Periodic imaging of internal region is not desirable because it complicates the treatment procedure. Also, in the case in which radiation is used to image internal region, periodic imaging using radiation is also not desirable because it increases the radiation dosage to the patient 628.

Figure 8:
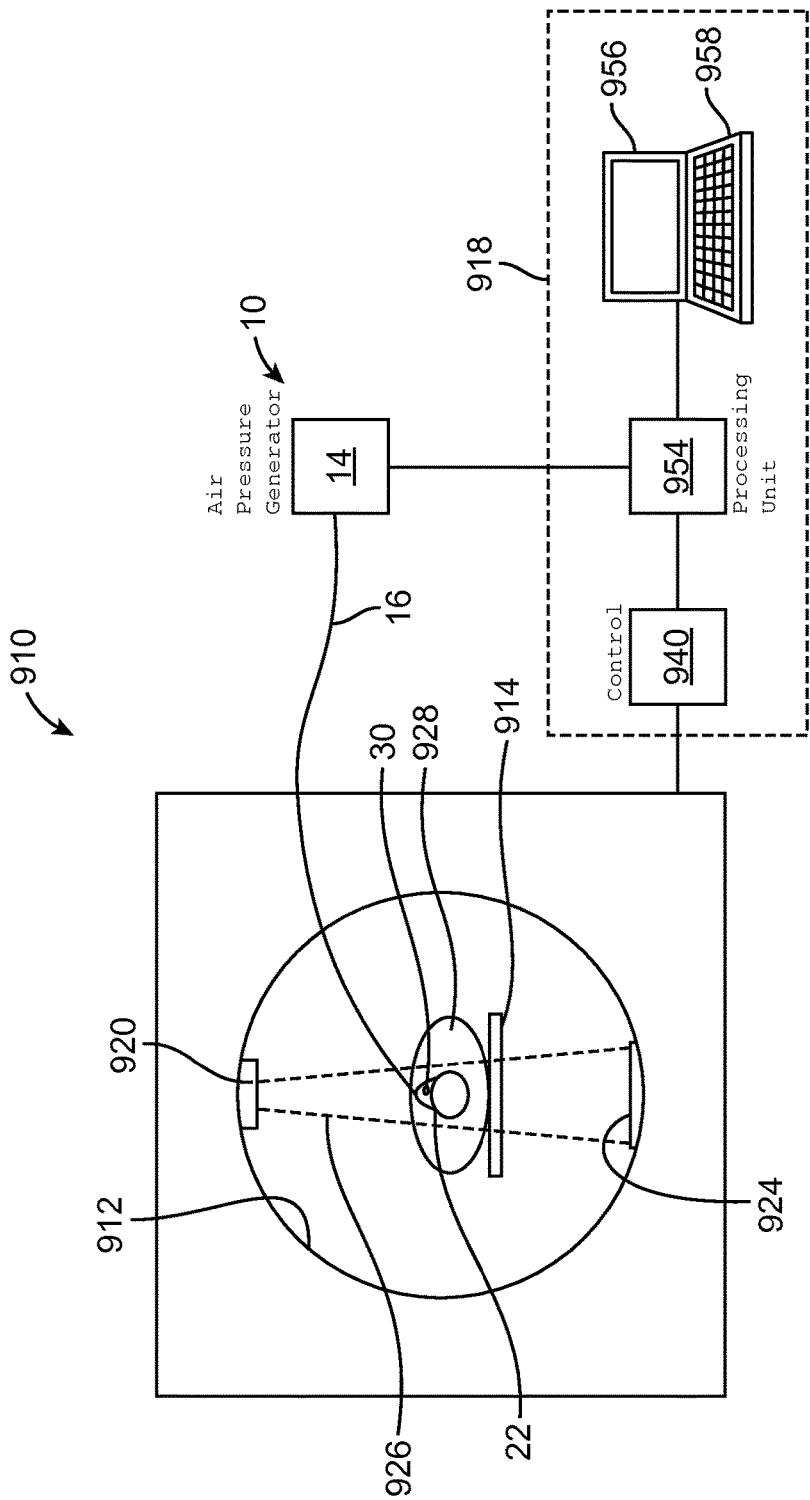
FIG. 8 illustrates another radiation system that uses the breathing monitoring system of FIG. 1 in accordance with other embodiments.

In further embodiments, instead of using the breathing monitoring system 10 with a device that has treatment capability, the breathing monitoring system 10 may be used with an imaging device. FIG. 8 illustrates a computed tomography system 910 that is used with the breathing monitoring system 10 in accordance with some embodiments. The system 910 includes a gantry 912, and a support 914 for supporting a patient 928. The gantry 912 includes an x-ray source 920 that projects a beam 926 of x-rays towards a detector 924 on an opposite side of the gantry 912 while the patient 928 is positioned at least partially between the x-ray source 920 and the detector 924. By means of non-limiting examples, the beam of x-rays can be a cone beam or a fan beam. The detector 924 has a plurality of sensor elements configured for sensing a x-ray that passes through the patient 928. Each sensor element generates an electrical signal representative of an intensity of the x-ray beam as it passes through the patient 928.

The system 910 also includes a control system 918. In the illustrated embodiments, the control system 918 includes a processing unit 954, such as a computer processor, coupled to a control 940. The control system 918 may also include a monitor 956 for displaying data and an input device 958, such as a keyboard or a mouse, for inputting data. The operation of the radiation source 920 and the gantry 912 are controlled by the control 940, which provides power and timing signals to the radiation source 920, and controls a rotational speed and position of the gantry 912, based on signals received from the processing unit 954. Although the control 940 is shown as a separate component from the gantry 912 and the processing unit 954, in alternative embodiments, the control 940 can be a part of the gantry 912 or the processing unit 954. The processing unit 954 may be the processing unit 34, or a separate processing unit that is different from the processing units 34. Also, in some embodiments, the screen 956 may be the screen 42, and the input device 958 may be the input device 44 of FIG. 1. In other embodiments, the screen 956 and the input device 958 may be different from the screen 42 and the input device 44 of FIG. 1.

It should be noted that the system 910 is not limited to the configuration described above, and that the system 910 may have other configurations in other embodiments. For example, in other embodiments, the system 910 may have a different shape. In other embodiments, the radiation source 920 of the system 910 may have different ranges of motions and/or degrees of freedom. For example, in other embodiments, the radiation source 920 may be rotatable about the patient 928 completely through a 360° range, or partially through a range that is less than 360°. Also, in other embodiments, the radiation source 920 is translatable relative to the patient 928. Further, the radiation source 920 is not limited to delivering diagnostic energy in the form of x-ray, and may deliver treatment energy for treating a patient.

During a scan to acquire x-ray projection data (i.e., CT image data), the gantry 912 rotates about the patient 928 at different gantry angles, so that the radiation source 920 and the imager 924 may be used to obtain images at different gantry angles. As the system 910 is operated to obtain images at different gantry angles, the patient 928 is breathing. Thus, the resulting images at different gantry angles may correspond to different phases of a breathing cycle for the patient 928. After the scan is completed, the projection images at different gantry angles are stored, e.g., in a memory (such as a non-transitory medium), and the projection images are processed to sort the images so that images at different gantry angles that correspond to a same phase of a breathing cycle are binned (e.g., associated with each other). The binned images for a specific phase of a respiratory cycle can then be used to generate a reconstructed three-dimensional CT image for that phase.

Figure 9:
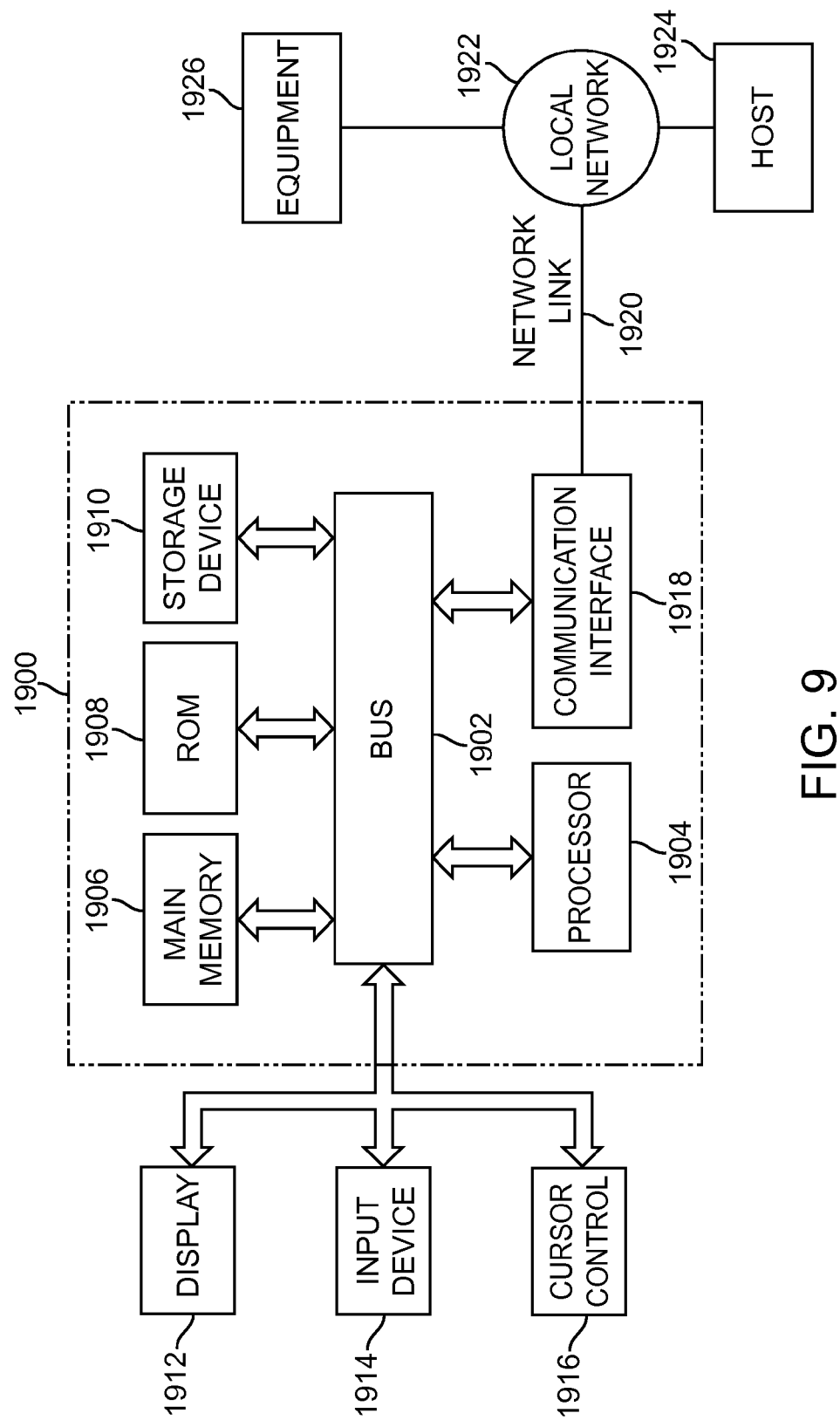
FIG. 9 is a block diagram of a computer system architecture, with which embodiments described herein may be implemented.

In some embodiments, when using the system 910 of FIG. 9, the radiation source 920 is rotated about the patient 928 to deliver diagnostic (imaging) radiation from a plurality of gantry angles. As radiation is being delivered to the patient 928, the breathing monitoring system 10 of FIG. 1 may be used to obtain the breathing signals for binning the images. For example, as images are being obtained using the system 910 to obtain projection images at different gantry angles, the signal values from the sensor 30 of the breathing monitoring system 10 are stored in the non-transitory medium. The signal values may be stored together with their corresponding time points at which the signal values are obtained. After or during the imaging session, the signal values may be processed by the processing unit 954 to determine corresponding phases for the signal values. For example, when a projection image is obtained at a certain gantry angle, the sensor 30 may sense a breathing characteristic having a value of "34", and the processing unit 954 may determine that such sensor signal value has a corresponding phase value of 15°. Also, a respiratory cycle may be divided into 6 phase bins—i.e., bin 1 for phases 0°-60°, bin 2 for phases 60°-120°, bin 3 for phases 120°-180°, bin 4 for phases 180°-240°, bin 5 for phases 240°-300°, and bin 6 for phases 300°-360°. In the above example, the projection image (that is obtained when the signal value of 34 having the corresponding phase value of 15° is obtained) is then binned into bin 1 because it cover phases 0°-60°. Thus, the breathing monitoring system 10 may be used to bin images (during an image session, or after an image session). After the images are binned into different phase bins, images that are within the same phase bin may then be used to reconstruct a CT image for that phase bin. In some embodiments, the reconstructed CT images for the different phase bins may be displayed in a sequence to form a video. In other example, the number of bins may be more than six or less than six.

In some embodiments, in addition to, or instead of, using the breathing monitoring system 10 to determine breathing signals for binning projection images, the breathing monitoring system 10 may be used to control the imaging device. For example, in some embodiments, the processing unit 954 processes the signals from the sensor 30 to determine breathing amplitudes of the patient 928, and then gates the delivery of the imaging radiation based on the amplitudes. For example, the processing unit 954 may cause the radiation source 920 to deliver radiation, or to stop a delivery of radiation, when the determined amplitude is within a prescribed amplitude range. In other embodiments, the processing unit 954 processes the signals from the sensor 30 to determine respiratory phases of the patient 928, and then gates the delivery of the radiation based on the respiratory phases. For example, the processing unit 954 may cause the radiation source 920 to deliver radiation, or to stop a delivery of radiation, when the determined phase is within a prescribed phase range. In other embodiments, instead of, or in addition to, controlling the delivery of radiation, the processing unit 954 may be configured to control the gantry 912 (e.g., stop, accelerate, or decelerate the gantry 912), and/or to position the patient support 914, based on the determined amplitude and/or phase.

In other embodiments of a method of using the system 10 with the radiation system 910, the processing unit 954 is configured to detect non-periodicity in the patient's 928 breathing based on signals received from the sensor 30. When the processing unit 954 determines that there is non-periodicity in the patient's 928 breathing, the processing unit 954 may generate a signal (e.g., a beam-stop signal) to cause the radiation source 920 to stop delivering radiation, a signal to control a motion of the gantry 912 (e.g., to stop the gantry, decelerate the gantry 912, or accelerate the gantry 912), and/or a signal to position the patient support 914.

As illustrated in the above embodiments, the breathing monitoring system 10 is advantageous because it may reduce a total amount of radiation dose delivered to the patient by considering breathing of the patient in the delivery of radiation. Also, in some embodiments, the breathing monitoring system 10 and methods described herein may be used to synchronize patient's respirations with a diagnostic imaging procedure to thereby reduce or eliminate motion artifact characteristics in various imaging techniques, including but not limited to CT, MRI, PET, SPECT, PET-CT, etc.

It should be noted that the breathing monitoring system 10 is not limited to being used with a radiation delivery device, and may be used with other medical devices, which may or may not be configured to deliver radiation.

Also, in one or more embodiments, the breathing monitoring system 10 may be configured to detect an end of inspiration (or beginning of exhalation) by using a sensor (e.g., pressure sensor, flow sensor, etc.) to detect resistance to filling. For example, if the sensor value has reached certain limit (e.g., the sensed pressure value may reach a maximum limit, or the sensed flow value in the inhale direction may reach a minimum limit), then the processing unit in the breathing monitoring system 10 may determine that the patient has reached an end of inspiration. In such cases, the system 10 may reduce the airflow/pressure to allow elastic recoil of the chest for expiration. Similarly, the system 10 may be configured to detect an end of exhalation (or beginning of inspiration) by using the sensor. For example, if the sensor value has reached certain limit (e.g., the sensed pressure value may reach a minimum limit, or the sensed flow value in the exhale direction may reach a minimum limit), then the processing unit in the breathing monitoring system 10 may determine that the patient has reached an end of exhalation. In such cases, the system 10 may increase airflow/pressure to provide support for inspiration. In some embodiments, the various limits for determining end of inspiration, beginning of exhalation, beginning of inspiration, and end of exhalation may be predetermined and set in the system 10. In other embodiments, one or more of the limits may be selectively set by a user of the system 10. Also, in one or more embodiments, the amount of airflow or pressure provided by the system 10 to support an inhalation, and/or the amount of airflow or pressure provided by the system 10 to support an exhalation, may be fixed in the system 10 or selectively set by a user of the system 10. It should be noted that the breathing monitoring system 10 is not limited to the examples of the functions described herein, and that other types of breathing system 10 may be used in other embodiments.

In addition, in some embodiments, the system 10 may be used to semi-control the patient's breathing so that the patient's breathing occurs in a predictable manner during an imaging procedure and/or a treatment procedure. For example, in some embodiments, the timing for initiating an inhale phase and/or an exhale phase may be determined by the patient, but the rest of the breathing pattern (e.g., speed of exhaling, speed of inhaling, etc.) may be achieved at least partially using the breathing monitoring system 10. For example, in some embodiments, a breathing cycle period, period length for inhalation, period length for exhalation, or any combination of the foregoing, may be entered or set in the breathing monitoring system 10. In such cases, the system 10 may be configured to provide different amount of airflow/pressure at different time points to achieve certain exhaling and/or inhaling speed based on any of the above information. In other embodiments, the system 10 may be configured to provide more control for the patient's breathing. For example, in other embodiments, the system 10 may be configured to determine when inhalation begins and/or ends, and when exhalation begins and/or ends. In further embodiments, the system 10 may be configured to allow the patient to control most of his/her breathing. In such cases, the system 10 may provide airway pressure support based on the patient's breathing pattern throughout the breathing cycle. In still further embodiments, the system 10 may be configured to control most or all of the patient's breathing. For example, in some embodiments, the system 10 may be configured to take over the breathing function of the patient and control a timing of the inhale phase for the patient. In some embodiments, the system 10 may also control a timing of the exhale phase. Also, in some embodiments, when the system 10 takes over the control of most or all of the patient's breathing, the patient may be intubated with one end of the tube 16 inserted into the mouth of the patient.

Furthermore, in one or more embodiments, the breathing monitoring system 10 may be used by patient who may or may not need any positive airway pressure support. For example, while patient who has breathing condition may benefit from the use of the breathing monitoring system 10 because it provides positive airway pressure for the patient, patient who does not have any breathing condition may also use the system 10. Also, in some embodiments, the breathing monitoring system 10 may provide air flow having a regular amount of oxygen concentration. In other embodiments, the breathing monitoring system 10 may be configured to provide airflow with an increased amount of oxygen concentration. For example, in some embodiments, a tank of concentrated oxygen may be fluidly coupled to the tube 16, so that when airflow/air pressure is created in the tube 16 by the breathing device, air with an increased amount of oxygen will be delivered to the patient. Thus, as used in this specification, the term "air", or similar terms (such as "airflow", "air pressure", etc.) is not limited to gas having a normal amount of oxygen concentration, but may also refer to any gas having any amount of oxygen concentration.

Computer System Architecture

FIG. 9 is a block diagram that illustrates an embodiment of a computer system 1900 upon which an embodiment of the invention may be implemented. Computer system 1900 includes a bus 1902 or other communication mechanism for communicating information, and a processor 1904 coupled with the bus 1902 for processing information. The processor 1904 may be an example of the processing unit 34 of FIG. 1, or another processor that is used to perform various functions described herein. In some cases, the computer system 1900 may be used to implement the processor 14 (or other processors described herein). The computer system 1900 also includes a main memory 1906, such as a random access memory (RAM) or other dynamic storage device, coupled to the bus 1902 for storing information and instructions to be executed by the processor 1904. The main memory 1906 also may be used for storing temporary variables or other intermediate information during execution of instructions to be executed by the processor 1904. The computer system 1900 further includes a read only memory (ROM) 1908 or other static storage device coupled to the bus 1902 for storing static information and instructions for the processor 1904. A data storage device 1910, such as a magnetic disk or optical disk, is provided and coupled to the bus 1902 for storing information and instructions.

The computer system 1900 may be coupled via the bus 1902 to a display 1912, such as a cathode ray tube (CRT) or a flat panel, for displaying information to a user. An input device 1914, including alphanumeric and other keys, is coupled to the bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The computer system 1900 may be used for performing various functions (e.g., calculation) in accordance with the embodiments described herein. According to one embodiment, such use is provided by computer system 1900 in response to processor 1904 executing one or more sequences of one or more instructions contained in the main memory 1906. Such instructions may be read into the main memory 1906 from another computer-readable medium, such as storage device 1910. Execution of the sequences of instructions contained in the main memory 1906 causes the processor 1904 to perform the process steps described herein. One or more processors in a multi-processing arrangement may also be employed to execute the sequences of instructions contained in the main memory 1906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1904 for execution. Such a medium may take many forms, including but not limited to, non-volatile media, volatile media, and transmission media. Non-volatile media includes, for example, optical or magnetic disks, such as the storage device 1910. A non-volatile medium may be considered as an example of a non-transitory medium. Volatile media includes dynamic memory, such as the main memory 1906. A volatile medium may be considered as another example of a non-transitory medium. Transmission media includes coaxial cables, copper wire and fiber optics, including the wires that comprise the bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1904 for execution. For example, the instructions may initially be carried on a magnetic disk of a remote computer. The remote computer can load the instructions into its dynamic memory and send the instructions over a telephone line using a modem. A modem local to the computer system 1900 can receive the data on the telephone line and use an infrared transmitter to convert the data to an infrared signal. An infrared detector coupled to the bus 1902 can receive the data carried in the infrared signal and place the data on the bus 1902. The bus 1902 carries the data to the main memory 1906, from which the processor 1904 retrieves and executes the instructions. The instructions received by the main memory 1906 may optionally be stored on the storage device 1910 either before or after execution by the processor 1904.

The computer system 1900 also includes a communication interface 1918 coupled to the bus 1902. The communication interface 1918 provides a two-way data communication coupling to a network link 1920 that is connected to a local network 1922. For example, the communication interface 1918 may be an integrated services digital network (ISDN) card or a modem to provide a data communication connection to a corresponding type of telephone line. As another example, the communication interface 1918 may be a local area network (LAN) card to provide a data communication connection to a compatible LAN. Wireless links may also be implemented. In any such implementation, the communication interface 1918 sends and receives electrical, electromagnetic or optical signals that carry data streams representing various types of information.

The network link 1920 typically provides data communication through one or more networks to other devices. For example, the network link 1920 may provide a connection through local network 1922 to a host computer 1924 or to equipment 1926 such as a radiation beam source or a switch operatively coupled to a radiation beam source. The data streams transported over the network link 1920 can comprise electrical, electromagnetic or optical signals. The signals through the various networks and the signals on the network link 1920 and through the communication interface 1918, which carry data to and from the computer system 1900, are exemplary forms of carrier waves transporting the information. The computer system 1900 can send messages and receive data, including program code, through the network(s), the network link 1920, and the communication interface 1918.

Although particular embodiments of the present inventions have been shown and described, it will be understood that it is not intended to limit the claimed inventions to the preferred embodiments, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. A medical apparatus, comprising:
    a breathing device comprising an air pressure generator for generating air pressure, a facemask defining a space, a tube for delivering the air pressure to the space defined by the facemask for a patient, and a sensor configured to sense a characteristic of a breathing of the patient; and
    a processing unit configured to receive an output from the sensor, the output comprising multiple sensor values at different respective time points, wherein the processing unit is further configured to determine metric values using the sensor values, and generate a control signal for controlling a medical device based at least in part on at least one of the metric values, wherein each of the metric values represents a degree of completeness of a breathing cycle.

2. The medical apparatus of claim 1, wherein the breathing device comprises a BPAP machine.

3. The medical apparatus of claim 1, wherein the breathing device comprises a CPAP machine.

4. The medical apparatus of claim 1, wherein the sensor comprises a pressure sensor or an airflow sensor.

5. The medical apparatus of claim 1, wherein the processing unit comprises a processor.

6. The medical apparatus of claim 1, wherein the medical device comprises a radiation machine, and the processing unit is configured to generate the control signal to control the radiation machine.

7. The medical apparatus of claim 6, wherein the radiation machine is configured to deliver diagnostic radiation for imaging the patient.

8. The medical apparatus of claim 6, wherein the radiation machine is configured to deliver treatment radiation for treating the patient.

9. The medical apparatus of claim 6, wherein the control signal is configured to control the medical device to perform one or more of: turning on a radiation beam, turning off the radiation beam, rotating a gantry of the radiation machine, operating a collimator, operating a patient support, and adjusting a dose rate.

10. The medical apparatus of claim 1, wherein the medical device comprises a collimator, and the processing unit is configured to generate the control signal to control the collimator in synchronization with the breathing of the patient.

11. The medical apparatus of claim 1, wherein the medical device comprises an imaging device, and the processing unit is configured to generate the control signal to activate the imaging device.

12. The medical apparatus of claim 11, wherein the imaging device comprises a CT machine, a PET machine, a PET-CT machine, or a MRI machine.

13. The medical apparatus of claim 1, wherein the processing unit is configured to generate the control signal in real time to control the medical device.

14. The medical apparatus of claim 1, wherein the processing unit is also configured to obtain information from a device that is configured to determine a position of a part of the patient, and to correlate the position of the part of the patient with the sensed characteristic.

15. The medical apparatus of claim 14, wherein the position determined by the device is associated with a breathing motion of the patient.

16. The medical apparatus of claim 14, wherein the device that is configured to determine the position comprises a breathing monitoring device.

17. The medical apparatus of claim 1, wherein the air pressure generator is configured to generate the air pressure in response to a respiratory activity of the patient.

18. A medical method, comprising:
    providing a breathing device, the breathing device comprising an air pressure generator for generating air pressure, a facemask defining a space, a tube for delivering the air pressure to the space defined by the facemask for a patient, and a sensor;
    sensing a characteristic of a breathing of the patient using the sensor;
    receiving, by a processing unit, an output from the sensor, the output comprising multiple sensor values at different respective time points;
    determining, by the processing unit, metric values using the sensor values, wherein each of the metric values represents a degree of completeness of a breathing cycle; and
    generating a control signal to control a medical device based at least in part on at least one of the metric values, wherein the control signal is generated by the processing unit.

19. The medical method of claim 18, wherein the breathing device comprises a BPAP machine.

20. The medical method of claim 18, wherein the breathing device comprises a CPAP machine.

21. The medical method of claim 18, wherein sensor comprises a pressure sensor or an airflow sensor.

22. The medical method of claim 18, wherein the medical device comprises a radiation machine, and the control signal is generated to control the radiation machine.

23. The medical method of claim 22, wherein the radiation machine is configured to deliver diagnostic radiation for imaging the patient.

24. The medical method of claim 22, wherein the radiation machine is configured to deliver treatment radiation for treating the patient.

25. The medical method of claim 22, wherein the control signal is configured to control the medical device to perform one or more of: turning on a radiation beam, turning off the radiation beam, rotating a gantry of the radiation machine, operating a collimator, operating a patient support, and adjusting a dose rate.

26. The medical method of claim 18, wherein the medical device comprises a collimator, and the control signal is generated to control the collimator in synchronization with the breathing of the patient.

27. The medical method of claim 18, wherein the medical device comprises an imaging device, and the control signal is generated to activate the imaging device.

28. The medical method of claim 27, wherein the imaging device comprises a CT machine, a PET machine, a PET-CT machine, or a MRI machine.

29. The medical method of claim 18, wherein the control signal is generated in real time to control the medical device.

30. The medical method of claim 18, further comprising:
obtaining information from a device that is configured to determine a position of a part of the patient; and
correlating the position of the part of the patient with the sensed characteristic.

31. The medical method of claim 18, wherein the air pressure generator is configured to generate the air pressure in response to a respiratory activity of the patient.

32. A medical apparatus, comprising:
a breathing device configured to provide air pressure, the breathing device comprising an air pressure generator for generating the air pressure, a facemask defining a space, and a tube for delivering the air pressure to the space defined by the facemask for a patient;
wherein the breathing device comprises a sensor configured to sense a characteristic associated with a breathing of the patient;
a processing unit configured to receive an output from the sensor, the output comprising multiple sensor values at different respective time points, wherein the processing unit is further configured to determine metric values using the sensor values, and generate a control signal to control a medical device based at least in part on at least one of the metric values, wherein each of the metric values represents a degree of completeness of a breathing cycle, and wherein the medical device is configured to provide a medical benefit that is different from that of the breathing device; and
a non-transitory medium for storing data associated with the sensed characteristic at the multiple time points.

33. The medical apparatus of claim 32, wherein the breathing device comprises a BPAP machine.

34. The medical apparatus of claim 32, wherein the breathing device comprises a CPAP machine.

35. The medical apparatus of claim 32, wherein the sensor comprises a pressure sensor or an airflow sensor.

36. The medical apparatus of claim 32, wherein the sensor is configured to sense airway pressure or airflow as the characteristic; and
wherein the data comprises:
airway pressure values or airflow values provided from the sensor, and
time points corresponding to the respective airway pressure values or airflow values.

37. The medical apparatus of claim 32, wherein the medical device comprises a radiation machine, and the processing unit is configured to generate the control signal to control the radiation machine.

38. The medical apparatus of claim 37, wherein the radiation machine is configured to deliver diagnostic radiation for imaging the patient.

39. The medical apparatus of claim 37, wherein the radiation machine is configured to deliver treatment radiation for treating the patient.

40. The medical apparatus of claim 37, wherein the control signal is configured to control the medical device to perform one or more of: turning on a radiation beam, turning off the radiation beam, rotating a gantry of the radiation machine, operating a collimator, operating a patient support, and adjusting a dose rate.

41. The medical apparatus of claim 32, wherein the processing unit is configured to generate the control signal in real time to control the medical device.

42. The medical apparatus of claim 32, further comprising a treatment planning unit configured to determine a parameter of a treatment plan using the data associated with the sensed characteristic, wherein the treatment plan is configured for use by the medical device.

43. The medical apparatus of claim 32, wherein the processing unit is also configured to obtain information from a device that is configured to determine a position of a part of the patient, and to correlate the position of the part of the patient with the sensed characteristic.

44. The medical apparatus of claim 43, wherein the position determined by the device is associated with a breathing motion of the patient.

45. The medical apparatus of claim 43, wherein the device that is configured to determine the position comprises a breathing monitoring device.

46. The medical apparatus of claim 32, wherein the air pressure generator is configured to generate the air pressure in response to a respiratory activity of the patient.

47. A medical method, comprising:
providing a breathing device, the breathing device comprising an air pressure generator for generating air pressure, a facemask defining a space, a tube for delivering the air pressure to the space defined by the facemask for a patient, and a sensor;
sensing a characteristic associated with a breathing of the patient using the sensor;
receiving, by a processing unit, an output from the sensor, the output comprising multiple sensor values at different respective time points;
determining, by the processing unit, metric values using the sensor values, wherein each of the metric values represents a degree of completeness of a breathing cycle; and
generating a control signal to control a medical device based at least in part on at least one of the metric values, wherein the medical device is configured to provide a medical benefit that is different from that of the breathing device, and wherein the control signal is generated by the processing unit; and
storing data associated with the sensed characteristic in a non-transitory medium.

48. The medical method of claim 47, wherein the breathing device comprises a BPAP machine.

49. The medical method of claim 47, wherein the breathing device comprises a CPAP machine.

50. The medical method of claim 47, wherein the sensor comprises a pressure sensor or an airflow sensor.

51. The medical method of claim 47, wherein the data comprises:

airway pressure values or airflow values provided from the sensor, and time points corresponding to the respective airway pressure values or airflow values.

52. The medical method of claim 47, further comprising determining a parameter of a treatment plan using the stored data, wherein the treatment plan is configured for use by the medical device.

53. The medical method of claim 52, wherein the treatment plan comprises a radiation treatment plan.

54. The medical method of claim 47, wherein the medical device comprises a radiation machine.

55. The medical method of claim 54, wherein the radiation machine comprises a radiation diagnostic machine.

56. The medical method of claim 54, wherein the radiation machine comprises a radiation treatment machine.

57. The medical method of claim 54, wherein the act of controlling the medical device comprises one or more of: turning on a radiation beam, turning off the radiation beam, rotating a gantry of the radiation machine, operating a collimator, operating a patient support, and adjusting a dose rate.

58. The medical method of claim 47, further comprising:
obtaining information from a device that is configured to determine a position of a part of the patient; and
correlating the position of the part of the patient with the sensed characteristic.

59. The medical method of claim 47, wherein the air pressure generator is configured to generate the air pressure in response to a respiratory activity of the patient.

* * * * *